US008887402B2

(12) United States Patent
Doppel et al.

(10) Patent No.: US 8,887,402 B2
(45) Date of Patent: Nov. 18, 2014

(54) MEASURING DEVICE FOR DETERMINING A LEG-AND-FOOT LENGTH FOR MEASUREMENT OF STOCKINGS, IN PARTICULAR MEDICAL COMPRESSION STOCKINGS

(75) Inventors: Wiebke Doppel, Kulmbach (DE); Beate Neugebauer, Bayreuth (DE)

(73) Assignee: Medi GmbH & Co. KG, Bayreuth (DE)

( * ) Notice: Subject to any disclaimer, the term of this patent is extended or adjusted under 35 U.S.C. 154(b) by 41 days.

(21) Appl. No.: 13/462,912

(22) Filed: May 3, 2012

(65) Prior Publication Data
US 2012/0304476 A1 Dec. 6, 2012

(30) Foreign Application Priority Data

Jun. 6, 2011 (DE) .......................... 10 2011 104 706

(51) Int. Cl.
*G01B 5/02* (2006.01)
*A61B 5/107* (2006.01)

(52) U.S. Cl.
CPC .................................... *A61B 5/1072* (2013.01)
USPC .............................................. 33/2 A; 33/512

(58) Field of Classification Search
CPC .............. D06H 3/16; G01B 3/04; G01B 3/56; G01B 3/563; A41H 1/02; A41H 1/04; A41H 9/02; A41H 31/00; A61B 5/1072; A61B 5/107; A01K 97/00; A01K 29/00; A01K 61/001; B43L 7/12; B43L 7/005; B43L 9/00; B43L 7/00; B43L 7/007; B43L 7/02
USPC ................................ 33/2 A, 8, 511, 512, 495
See application file for complete search history.

(56) References Cited

U.S. PATENT DOCUMENTS

| 1,577,991 | A | * | 3/1926 | Victorius ........................ 33/2 A |
| 1,974,085 | A | * | 9/1934 | Shields et al. .................. 33/512 |
| 2,125,530 | A | * | 8/1938 | Verdier ............................... 33/8 |
| 2,537,417 | A | * | 1/1951 | Merske ......................... 206/281 |
| 2,734,270 | A | * | 2/1956 | Finnegan ............................ 33/8 |
| 4,203,227 | A | * | 5/1980 | Giroux ............................ 33/458 |
| 4,674,189 | A | * | 6/1987 | Parisi et al. ......................... 33/8 |
| D387,689 | S | * | 12/1997 | Sharon et al. .................. D10/71 |
| 5,915,810 | A | * | 6/1999 | Cameron ....................... 33/809 |
| 6,003,235 | A | * | 12/1999 | Chen ............................... 33/512 |
| 6,745,481 | B1 | * | 6/2004 | Faircloth ........................ 33/2 A |

(Continued)

FOREIGN PATENT DOCUMENTS

| DE | 202007017259 U1 | 2/2008 |
| EP | 2389861 A1 | 11/2011 |
| SU | 891086 | 12/1981 |
| WO | 9314728 A1 | 8/1993 |

OTHER PUBLICATIONS

Russian Office Action issued Mar. 28, 2014 for corresponding Application No. 2012122626/12.

(Continued)

*Primary Examiner* — Yaritza Guadalupe-McCall
(74) *Attorney, Agent, or Firm* — Lucas & Mercanti, LLP (57) ABSTRACT

Measuring device for determining a leg length for measurement of stockings, in particular medical compression stockings, comprising a base plate with a foot-receiving surface and, arranged vertically thereon, a measurement board, wherein the measurement board (6), which can be mounted releasably on the base plate (2), is composed of a plurality of releasably connectable board sections (6*a*, 6*b*, 6*c*, 6*d*).

38 Claims, 4 Drawing Sheets

(56) References Cited

U.S. PATENT DOCUMENTS

| | | | |
|---|---|---|---|
| 6,964,110 B2 * | 11/2005 | Shapiro | 33/458 |
| 7,103,983 B2 * | 9/2006 | Lehavi | 33/512 |
| 7,200,951 B2 * | 4/2007 | O'Connor | 33/528 |
| 7,770,301 B1 * | 8/2010 | Grandberry et al. | 33/494 |
| 2005/0155246 A1 | 7/2005 | Montagnino | |
| 2006/0005408 A1 * | 1/2006 | Fernand | 33/471 |
| 2008/0289199 A1 * | 11/2008 | Healey | 33/195 |
| 2012/0304476 A1 * | 12/2012 | Doppel et al. | 33/700 |

OTHER PUBLICATIONS

English translation of Russian Office Action issued Mar. 28, 2014 for corresponding Application No. 2012122626/12.

* cited by examiner

MEASURING DEVICE FOR DETERMINING A LEG-AND-FOOT LENGTH FOR MEASUREMENT OF STOCKINGS, IN PARTICULAR MEDICAL COMPRESSION STOCKINGS

This application claims the priority of DE 10 2011 104 706.2 filed Jun. 6, 2011, which is incorporated by reference herein.

The invention relates to a measuring device for determining a leg length for measurement of stockings, in particular medical compression stockings, comprising a base plate with a foot-receiving surface and, arranged vertically thereon, a measurement board.

Mainly on account of medical conditions affecting their veins, many people nave to wear special stockings, in particular medical compression stockings, which fit the leg exactly and build up a defined pressure profile (in accordance with RAL quality assurance). In these cases, it is necessary for the stockings, which are sometimes also customized items, to be adapted as exactly as possible to the circumference in question. To do this, a measuring device of the type described in the introduction is used, by means of which it is possible to very precisely determine the length of the leg and foot or of the area along which the stocking is intended to be placed. This area can be an area of the lower leg, if only a short stocking is to be fitted. However, if a long stocking or a stocking hose is to be fitted, the area can also cover the entire length of the leg up to the waist.

A known measuring device is composed of a base plate with a foot-receiving surface, on which the patient stands with the leg that is to be measured. On the rear face of the base plate, a measurement board is provided which is arranged vertically with respect to the foot-receiving surface and which, when the patient is standing on the base plate, extends behind the leg. A measurement scale, for example a centimeter rule with a suitably fine millimeter subdivision on the left-hand side, is provided both on the measurement board and also on the foot part. The length of the leg section that is to be covered by the stocking can be exactly determined in this way. On the right-hand side, the measurement scale is encoded in individual barcodes for digital transmission to an electronic measuring system. By means of a flexible measurement tape, it is also possible, at suitable heights, to determine the circumference at defined anatomical measurement points, such that, overall, the use of this measuring device permits very precise determination of the leg dimensions. Such measuring devices are used, for example, in general practices, clinics or medical supply stores, or, if appropriate, also directly at the patient's home.

A measuring device of this kind is made collapsible such that it can also be easily transported. That is to say, the base plate and the measurement board are pivotably connected to each other by a hinge. Moreover, to be able to reduce the length of the measurement board, the latter is also provided with at least one hinge allowing it to be folded up. When the parts have been pivoted open, they can be fixed in the pivoted-open position by means of lateral slides, usually made of plastic, which connect two parts.

Although the hinges allow the measuring device to be folded into a small format, there is always the problem, during unfolding and folding, of fingers possibly getting caught and of the operator therefore sustaining an injury. Moreover, the slides that are used to fix the parts are very easily damaged, since they can easily break off if handled carelessly.

Therefore, the object of the invention is to make available a measuring device that is improved compared to the previously known measuring devices.

In a measuring device of the type mentioned at the outset, this object is achieved, according to the invention, in that the measurement board, which can be mounted releasably on the base plate, is composed of a plurality of releasably connectable board sections.

The measuring device according to the invention can be divided into several parts, since all of the individual parts of the measuring device are releasably connectable to each other. That is to say, the measurement board can be released from the base plate for transportation, and the measurement board, composed of a plurality of individual board sections, can also be dismantled into these individual board sections. Therefore, in order to assemble the device, all that needs to be done is to connect the individual parts to each other, in other words fit the base plate and the first board section together, and then attach one or more further board sections to form the measurement board. A pivot connection, in which the parts are therefore connected to each other with positive locking, is not provided according to the invention, and as a result there is no longer a danger of injury, since the board sections are releasably connectable to each other, and one board section is releasably connectable to the base plate, preferably by plug or slide connections, whereby elements are therefore securely plugged or slid into each other. There is also no need for structural parts that prevent renewed folding-up, since good stability is already afforded by the plug or slide connections. In addition, it is also possible for the measurement board to be "built up" only as high as is necessary. If the measurement board is composed, for example, of a maximum of four board sections, then, if the leg is to be measured only up to the knee, it is sufficient for only two board sections, for example, to be plugged or slid together, which is sufficient for the measurement task. If it is necessary to measure the entire leg up to the waist, all the board sections are interconnected to give the maximum length of the measurement board.

As has already been described, the releasable connection of the board sections to each other, and of one board section to the base plate, is effected by simple plug or slide connections. According to one development of this inventive concept, a plug connection can be made via one or more plug sections, which project from an end edge of the one board section or of the base plate, and one or more plug-section sockets, which are provided on an end edge of the other board section or of the base plate. The plug sections and the plug-section sockets expediently engage in each other with a form fit, such that a sufficient stability of the plugged structure is already obtained when the plug connections engage in each other.

An alternative to the plug connection is the slide connection. According to a development of this inventive alternative, a slide connection can be made via a spring-like slide section, which projects from an end edge of the one board section or of the base plate, and a slide groove, which is provided on an end edge of the other board section or of the base plate. In this inventive embodiment, therefore, two parts that are to be connected are, as it were, slid into each other from the side, for which purpose the end edges that are to be connected are again provided with corresponding connecting sections in the form of a projecting spring-like slide section on one part and a corresponding slide groove on the other part. Here too, slide section and slide groove preferably engage in each other with a form fit, so as to already ensure sufficient stability once they have been slid together. This connection possibility is also sufficiently simple, such that, in the same way as with the plug connection, the measuring device can be very easily constructed and dismantled. The plug connections or the slide connections can be coded, such that only defined board sections are connectable to each other or to the base plate. Such coding can be obtained by the shape and/or size and/or position of at least some of the plug sections and plug sockets or slide sections and slide sockets provided on the board sections and base plate being different. In this way, it is possible to ensure that only defined parts can be plugged onto each other or slid into each other, and any mix-up is avoided.

Although very good stability is already provided by the plugging together or sliding together, in particular with the form-fit engagement, it is proposed, in an expedient development of the invention, to use suitable fixing means for fixing two connected board sections and/or fixing one board section on the base plate. These fixing means can, for example, comprise retaining screws that extend through an opening on the one board section or the base plate and are to be screwed into a thread on the board section that is to be connected. Such a retaining screw, for example a screw provided with a knurled head, is pushed into the opening, for example from the direction of the longitudinal end face, and is screwed into a thread which, for example, is formed on a plug section that is fitted into the plug socket on the structural part having the opening. However, it would of course also be conceivable for the retaining screw to be introduced from the direction of the rear face into the opening located there and to be once again screwed into a thread on a plug section. The securing can be achieved in a similar way in a slide connection, in which case, for example, the thread would be provided on the spring-like slide section.

As an alternative to the use of a retaining screw and a thread, a fixing means can also comprise retaining pins that extend through an opening on the one board section or the base plate and are to be plugged into a socket on the board section that is to be connected. Therefore, no screwing takes place here, only a plugging-in of the retaining pin, such that a thread is not required. In this inventive embodiment, it is possible for the retaining pins, which are arranged captively on the respective part, to be mounted movably against a respective spring element, such that, when two board sections are joined together or one board section is joined to the base plate, the retaining pins are moved against the spring element and, on reaching the connection position, snap automatically into the sockets. That is to say, the user only has to insert the plug section or plug sections into the plug sockets, for example, and slide the parts together, whereupon, on reaching the end position, the retaining pin or retaining pins snap(s) into the sockets as a result of the restoring force of the until then pretensioned spring. Of course, the retaining pin or retaining pins can again be pulled out from this locked position against the spring in order to release the parts.

To ensure that the retaining pins, which are as it core forced by the spring into the closed position prior to the plugging together, can be moved outward during the sliding together, a development of the invention proposes that, in order to move a spring-mounted retaining pin against the spring element, a run-on bevel is provided on the board section having the socket. If the socket is located, for example, on the side of a plug section, the plug section can be provided on this side with the run-on bevel which, during the plugging together, engages the retaining pin and, upon further plugging together, forces the pin outward against the spring. When the end position is reached, the spring-mounted retaining pin snaps automatically into the socket.

A retaining pin can preferably be fixed in its release position with the spring element tensioned. If two parts that have been plugged together or slid together are to be released, the retaining pin must be pulled out from its snapped-in position. To ensure that the retaining pin does not have to be permanently held in order to pull the parts away from each other, it is possible to fix the retaining pin in the pulled-out release position, for example by simply turning it through 90°. This allows two connected parts to be easily released, even when, as is preferably provided according to the invention, corresponding fixing means, in this case preferably spring-mounted retaining pins, are provided on both sides.

To ensure that the fixing means do not protrude far at the sides, the fixing means in the form of the retaining screws or one retaining pins are, in the fixing position, preferably countersunk or bear on the measuring device in such a way that they do not jut out from the latter.

As has already been described, the fixing means are preferably provided on both longitudinal faces of the base plate or of the board sections, although this is not absolutely essential. Particularly in the design with slide connections, it is possible for the slide groove and the slide section not to extend across the full length but to stop before the respective end of the part, such that sliding together is possible only from one side. Since sliding all the way through is then not possible, fixing at only one location is sufficient.

The base plate and the board sections are preferably made of plastic, in particular polystyrene, which permits simple production and ensures safety against breaking.

This also provides the possibility of snaking the base plate sufficiently thin, preferably with a thickness of ≤1 cm. This is advantageous in the sense that a compensating plate does not have to be provided for the second leg, which compensating plate, in previously known measuring devices with relatively thick and in most cases hollow base plates, had to be used to avoid the patient standing at an angle. The thin design of the base plate as solid material is also advantageous in the sense that very heavy patients weighing over 100 kg can easily step onto the base plate. Moreover, the measurement board was made relatively wide (ca. 21 cm) so as also to permit precise measurement of quite large thigh circumferences.

The use of plastic as the material for producing the measuring device is advantageous in the sense that the parts can be easily imprinted, for example with screen print, and coating with clear varnish or a cover film and the like is easily possible in order in particular to protect the measurement board from dirt, scratching and the like, and also to cover the print, such that the latter cannot be damaged by cleaning with disinfecting agents. Knobs and the like are preferably arranged on the floor side such that the base plate can be positioned securely against slipping. However, the measuring device can be used both with the patient standing and also with the patient lying down, for example a patient lying on a hospital bed. The reason for this is that, as a result of the intended connection of parts by firm plugging together or sliding together, irregularities, for example in the hospital bed, do not adversely affect the measurement, since the measurement board is not thereby deformed.

Further advantages, features and details of the invention will become clear from the illustrative embodiment described below and by reference to the drawings, in which.

Figure 1:
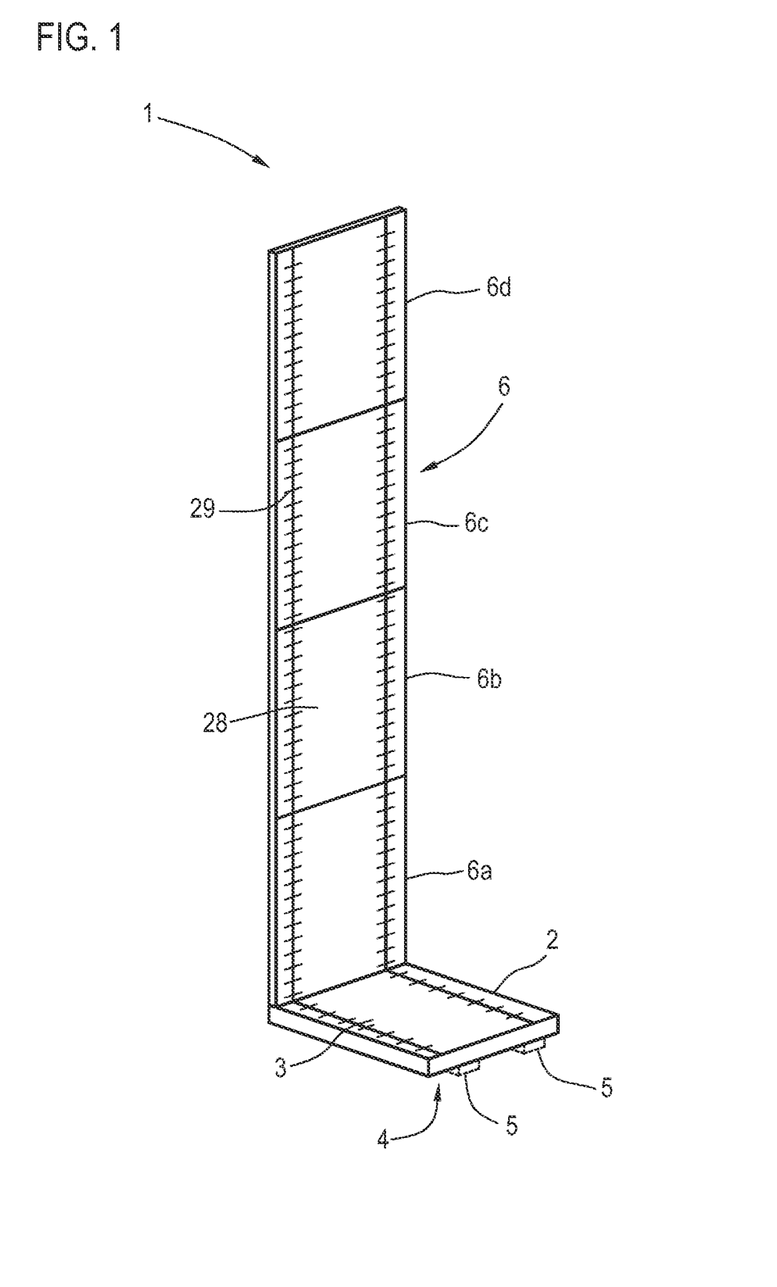
FIG. 1 shows a perspective view of a measuring device according to the invention.

FIG. 1 shows a measuring device 1 according to the invention for determining the length of a leg and foot, as is necessary for the measurement of stockings, in particular medical compression stockings. The measuring device 1 comprises a base plate 2 with a foot-receiving surface 3, on which the patient stands during the measurement procedure. Suitable antislipping supports 5, only indicated here by broken lines, are provided on the underside 4 of the base plate 2.

The measuring device 1 further comprises a measurement board 6, which is secured releasably on the rear end of the base plate 2. In the example shown, the measurement board 6 itself is composed of four separate board sections 6a, 6b, 6c and 6d, which are likewise connected releasably to each other. The releasable connection of said structural parts allows she measuring device 1 to be easily built up by plugging or sliding said parts together, as will be discussed in more detail below, and to be taken apart after use and dismantled into a compact format in which it can be easily transported. A length scale 29 is applied, for example printed, on the base plate 2 and on the surface 28 of the measurement board 6 facing the base plate 2 and is used to measure the length of the foot and leg. In the example shown, this length scale 29 is provided only locally, for example at the sides, but it can of course also be applied across the full width.

Figure 2:
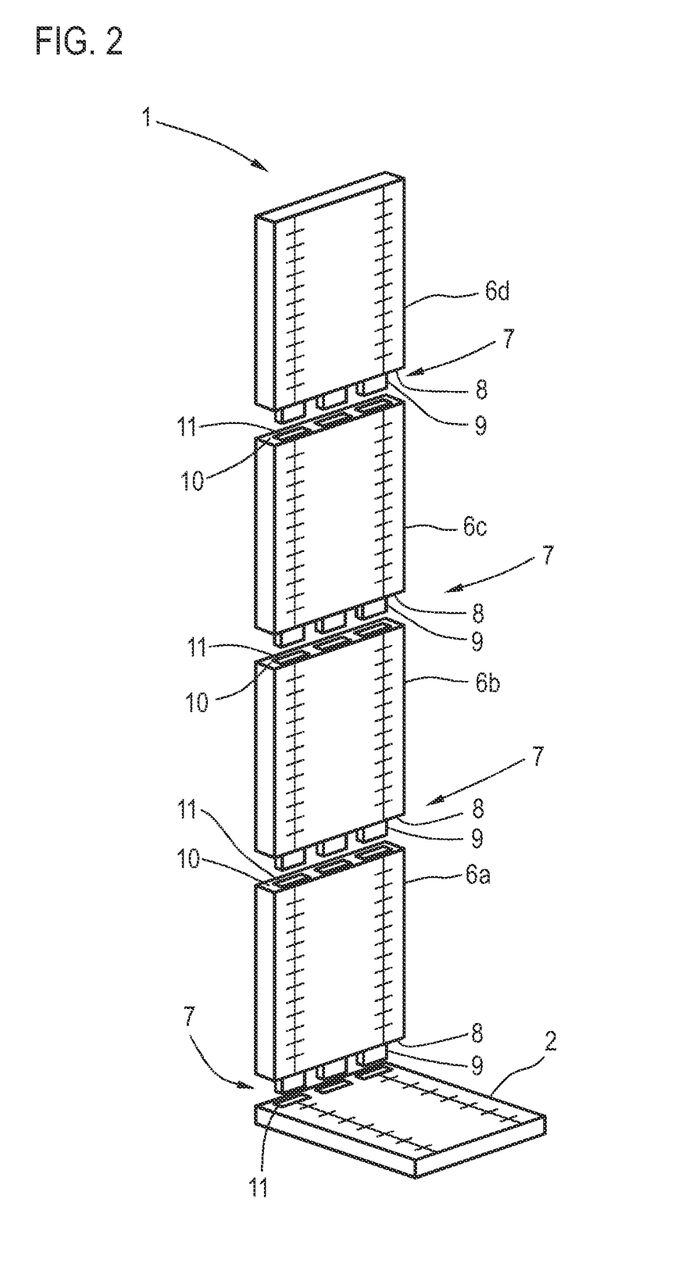
FIG. 2 shows an exploded view of the measuring device from FIG. 1.

FIG. 2 shows an exploded view of all the individual parts of the measuring device 1, namely the base part 2 and the four board sections 6a, 6b, 6c and 6d.

To be able to releasably connect the board sections 6a-6d to each other, and to be able to arrange the board section 6a releasably on the base plate 2, suitable plug connections 7 are formed, comprising plug sections 9, which project from the end faces 8 of the board sections 6a-6d, and plug sockets 11, which are formed on the base plate 2 and also on the opposite end faces 10 of the plug sections 6a-6c. In the example shown, the plug sections 9 and the plug sockets 11 are rectangular, in other words are adapted in shape to each other, such that a form-fit plug connection can be obtained. Other shapes (oval, round, etc.) are of course also conceivable. By corresponding different positions of the plug sections 9 and of the associated plug sockets 11, it is additionally possible to form a coding arrangement which ensures that only parts that belong to each other can be plugged together, that is to say, for example, only the board sections 6a and 6b can be plugged together, and it would be impossible to plug the board section 6c into the board section 6a, since the plug sections 9 of the plug seer ion 6c would not fit in the plug sockets 11 of the plug section 6a.

In any case, the measuring device 1 can therefore be very quickly assembled in situ, by simply plugging these shown parts together, and then dismantled again. In addition, the measuring device affords the advantage that the measurement board 6 need only be built to the height that is actually needed for the measurement procedure. For example, if only the length of the leg up to the knee is to be determined, in order to adapt a stocking that covers the lower leg, only the board sections 6a and 6b need be plugged together along with the base plate 2, whereas, if the whole leg is to be measured up to and including the waist, the two other board sections 6c and 6d are also plugged on.

Figure 3:
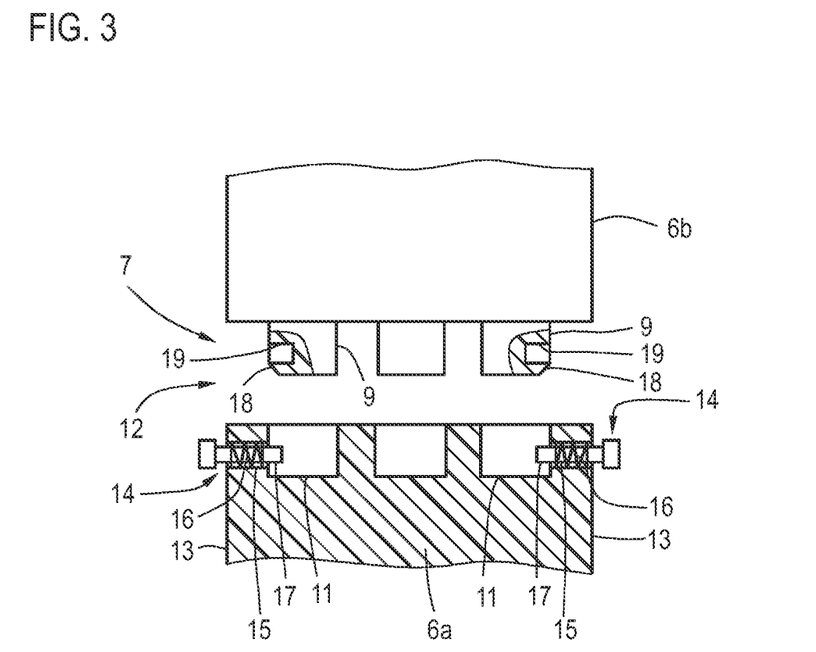
FIG. 3 shows an enlarged detail view illustrating the connection of two device parts in a first embodiment.

FIG. 3 snows how a plug connection 7, already having sufficient basic stability from the outset by virtue of the form-fit engagement, can be fixed such that the connected parts cannot be readily separated from each other. Fixing means 12 are provided for this purpose, in which respect, in the example shown, corresponding fixing means are arranged both on the left and also on the right. In the example shown, the fixing means comprise, on one structural part, in this case by way of example the board section 6a, retaining pins 14 which are arranged on the longitudinal faces 11 and which are received there in an opening 15, in which a spring element 16, in this case a helical spring, is also arranged. With their free end 17, the spring pins protrude into the adjacent plug socket 11. The spring pins 14 can be pulled out from the fixing position shown in FIG. 3, to which they are automatically brought via the spring element 16, counter to said spring element 16. However, they are secured against being removed. They can be locked in this pulled-out release position, for example by means of the spring pin 14 being turned slightly such that a locking mechanism engages, for example with a radial lug of the retaining pin 14 being burned against an abutment and the like, such that the spring element 16 cannot push the respective retaining pin 14 back. This locking mechanism is useful during the dismantling procedure, since the user is able to release the two retaining pins on the right and left using his hands, but is then no longer forced to hold them and instead can pull the board section 6b out in a simple manner.

At the time of assembly, the retaining pins 14 are located in the fixing position shown in FIG. 3, not least for transportation reasons. It is now possible, in this position, to plug the board section 6b on without having to pull out the retaining pins 14 (although this is readily possible by virtue of the locking possibility). For this purpose, the two lateral plug sections 9 have oblique run-on surfaces 18, and they each nave a socket 19 arranged transversely with respect to the latter. If the board section 6b is now plugged in, the plug sections 9 slide into the plug sockets 11 and, in the process, the run-on surfaces 18 make contact with the free end of the respective spring pin 14 and, by means of their oblique position, push the latter out as they are further inserted. When the board section 6b reaches the end position, the plug sections 9 thus lie as deep as possible in the plug sockets 11, and the free ends 17 of the retaining pins 14 thus snap automatically into the socket 19 under the action of the then relaxing spring elements 16 and fix the inserted board section 6b.

Figure 4:
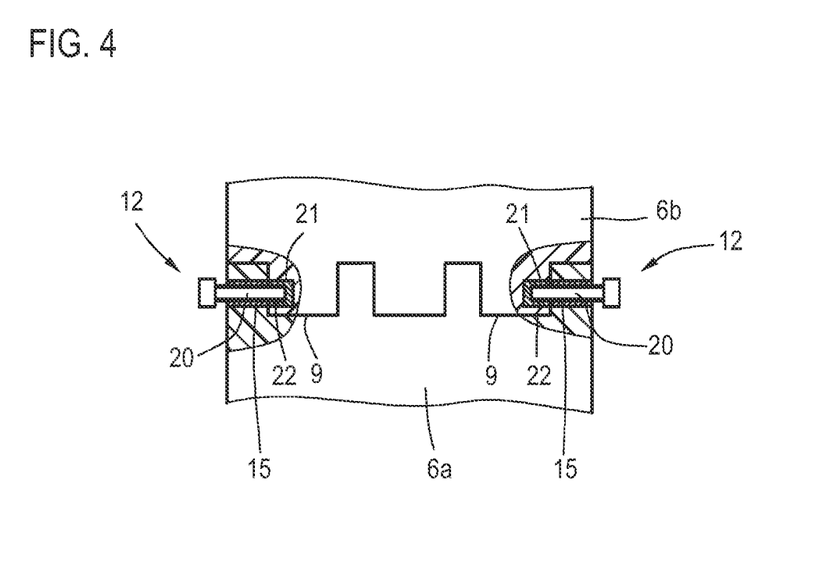
FIG. 4 shows an enlarged detail view illustrating the connection of two device parts in a second embodiment.

A further and alternative possibility of securing is shown in FIG. 4. Here too, fixing means 12 are provided, these being in the form of retaining screws 20. These again extend through a corresponding opening 15 on the board section 6a, also shown here as an example, and are fixed by being screwed with their thread 22 into a threaded sleeve 21, which is provided in the respective ping section 9. The screws 20 (like the retaining pins 14 too) have a suitably large head that can be easily gripped by hand, such that the screwing in and out (or pulling out in the case of the retaining pins 14) takes place correspondingly easily. However, in the respective fixing positions, the heads bear as closely as possible on the longitudinal faces of the measurement board, i.e. do not jut out from the latter.

Figure 5:
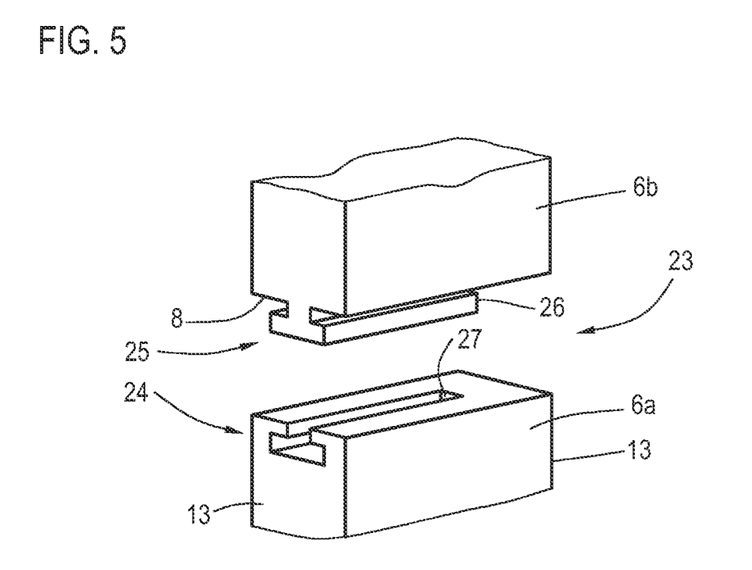
FIG. 5 shows an enlarged detail view illustrating the connection of two device parts in a third embodiment.

FIG. 5, finally, shows another illustrative embodiment of an arrangement by which parts are connected, here in the form of a slide connection 23. This form of connection is once again provided on all the parts that are to be connected (i.e. the base plate 2 and all the board sections 6a-6d), although once again only the board sections 6a and 6b are shown by way of example.

On the board section 6a, a slide groove 24 is formed, which extends horizontally from the longitudinal face 13 on the upper end of the board section. It is designed as a T-groove undercut on both sides. It does not extend across the full width of the board section but to just short of the end, so as to permit insertion only from the left side.

On the underside 8 of the board section 6b, a spring-like slide section 25 is formed whose cross-sectional form is adapted to the cross-sectional form of the slide groove 24 and is therefore also T-shaped. The slide section 25 also does not extend all the way to the end, such that an abutment is formed by the end face 26 of the slide section 25 and by the end 27 of the slide groove 24.

To connect the board sections to each other and to connect the board section 6a to the base plate 2, which has a corresponding slide groove 24, the parts simply have to be pushed into each other from the side. In this case too, the form-fit engagement ensures that sufficient stability is already obtained upon closure of the slide connection. Once again, fixing means 12 can additionally be provided, for example a retaining screw 20 screwed in from the right-hand longitudinal face 13 of the board section 6a, which retaining screw 20 is screwed into a threaded sleeve 21 formed on the end face 26 of the slide section 25.

The base plate 2 and the plug sections 6a-6d are preferably made of plastic, preferably polystyrene, and thus have good slide properties right from the outset, making the parts easy to plug or slide together.

The invention claimed is:

1. A measuring device for determining a leg length for a measurement of stockings, the measuring device comprising:
   a horizontal base plate comprising a foot-receiving surface; and
   a measurement board comprising a plurality of releasably connectable board sections, the measurement board adapted to be mounted releasably on the base plate in a vertical position and perpendicular to the base plate, wherein
   the base plate has printed thereon a first length scale for measuring a foot; and
   the measurement board has printed thereon a second length scale for measuring a leg.

2. The measuring device according to claim 1, wherein the board sections are releasably connectable to each other and to the base plate by plug or slide connections.

3. The measuring device according to claim 2, wherein a plug connection is made via one or more plug sections, which project from an end edge of a first board section or of the base plate, and one or more plug-section sockets, which are provided on an end edge of a second board section or of the base plate.

4. The measuring device according to claim 3, wherein the plug sections and the plug-section sockets engage in each other with a form fit.

5. The measuring device according to claim 2, wherein a slide connection is made via a spring-like slide section, which projects from an end edge of a first board section or of the base plate, and a slide groove, which is provided on an end edge of a second board section or of the base plate.

6. The measuring device according to claim 5, wherein the slide sections and the slide grooves engage in each other with a form fit.

7. The measuring device according to claim 1, wherein fixing means are provided for fixing two connected board sections and/or fixing one board section on the base plate.

8. The measuring device according to claim 7, wherein the fixing means comprise retaining screws that extend through an opening on a first board section or the base plate and are to be screwed into a thread on a second board section that is to be connected.

9. The measuring device according to claim 8, wherein the retaining screws or the retaining pins are, in the fixing position, countersunk or bear on the measurement board or the base plate.

10. The measuring device according to claim 7, wherein the fixing means comprise retaining pins that extend through an opening on a first board section or the base plate and are to be plugged into a socket on a second board section that is to be connected.

11. The measuring device according to claim 10, wherein the retaining pins are mounted movably against a spring element such that, when two board sections are joined together or one board section is joined to the base plate, the retaining pins are moved against the spring element and, on reaching the connection position, snap automatically into the sockets.

12. The measuring device according to claim 11, wherein, in order to move a spring-mounted retaining pin against the spring element, a run-on bevel is provided on the board section having the socket.

13. The measuring device according to claim 11, wherein the retaining pins can be fixed in their release position with the spring element tensioned.

14. The measuring device according to claim 7, wherein fixing means are provided on both longitudinal faces of the base plate or of the board sections.

15. The measuring device according claim 1, wherein the base plate and the board sections are made of plastic, in particular polystyrene.

16. The measuring device according to claim 1, wherein the base plate has a thickness of less than or equal to 1 cm.

17. A measuring device for determining a leg length for measurement of stockings, comprising:
   a base plate comprising a bottom surface adapted to maintain contact with a floor, and a top surface opposite the bottom surface, the top surface including a foot-receiving surface, and a plurality of plug sockets; and
   a measurement board mountable releasably on the base plate, the measurement board comprising a plurality of releasably connectable board sections, each board section comprising a first end, a second end, a plurality of plug sections projecting from the first end, and a plurality of plug sockets in the second end;
   wherein respective board sections are releasably connectable to each other by insertion of plug sections of a respective first board section into plug sockets of a respective second board section; and
   wherein at least one respective board section is releasably connectable perpendicularly to the base plate by insertion of plug sections of the at least one respective board section into the plug sockets of the base plate.

18. The measuring device according to claim 17, wherein fixing means are provided for fixing two connected board sections and/or fixing one board section on the base plate.

19. The measuring device according to claim 18, wherein the fixing means comprise retaining screws that extend through an opening on a first board section or the base plate and are to be screwed into a thread on a second board section that is to be connected.

20. The measuring device according to claim 19, wherein the retaining screws or the retaining pins are, in the fixing position, countersunk or bear on the measurement board or the base plate.

21. The measuring device according to claim 18, wherein the fixing means comprise retaining pins that extend through an opening on a first board section or the base plate and are to be plugged into a socket on a second board section that is to be connected.

22. The measuring device according to claim 21, wherein the retaining pins are mounted movably against a spring element such that, when two board sections are joined together or one board section is joined to the base plate, the retaining pins are moved against the spring element and, on reaching the connection position, snap automatically into the sockets.

23. The measuring device according to claim 22, wherein, in order to move a spring-mounted retaining pin against the spring element, a run-on bevel is provided on the board section having the socket.

24. The measuring device according to claim 22, wherein the retaining pins can be fixed in their release position with the spring element tensioned.

25. The measuring device according to claim 18, wherein fixing means are provided on both longitudinal faces of the base plate or of the board sections.

26. The measuring device according claim 17, wherein the base plate and the board sections are made of plastic, in particular polystyrene.

27. The measuring device according to claim 17, wherein the base plate has a thickness of less than or equal to 1 cm.

28. A measuring device for determining a leg length for measurement of stockings, comprising:
 a base plate comprising a bottom surface adapted to maintain contact with a floor, and a top surface opposite the bottom surface, the top surface including a first length scale printed thereon, and a foot-receiving surface; and
 a measurement board mountable releasably on the base plate in a vertical position perpendicular to the base plate, the measurement board comprising a plurality of releasably connectable board sections, each board section comprising a first end, a second end, a slide section on the first end, a slide groove on the second end, and a surface having a second length scale printed thereon;
 wherein respective board sections are releasably connectable to each other by insertion of a respective slide section of a first board section into a respective slide groove of a second board section.

29. The measuring device according to claim 28, wherein fixing means are provided for fixing two connected board sections and/or fixing one board section on the base plate.

30. The measuring device according to claim 29, wherein the fixing means comprise retaining screws that extend through an opening on a first board section or the base plate and are to be screwed into a thread on a second board section that is to be connected.

31. The measuring device according to claim 30, wherein the retaining screws or the retaining pins are, in the fixing position, countersunk or bear on the measurement board or the base plate.

32. The measuring device according to claim 29, wherein the fixing means comprise retaining pins that extend through an opening on a first board section or the base plate and are to be plugged into a socket on a second board section that is to be connected.

33. The measuring device according to claim 32, wherein the retaining pins are mounted movably against a spring element such that, when two board sections are joined together or one board section is joined to the base plate, the retaining pins are moved against the spring element and, on reaching the connection position, snap automatically into the sockets.

34. The measuring device according to claim 33, wherein, in order to move a spring-mounted retaining pin against the spring element, a run-on bevel is provided on the board section having the socket.

35. The measuring device according to claim 33, wherein the retaining pins can be fixed in their release position with the spring element tensioned.

36. The measuring device according to claim 29, wherein fixing means are provided on both longitudinal faces of the base plate or of the board sections.

37. The measuring device according claim 28, wherein the base plate and the board sections are made of plastic, in particular polystyrene.

38. The measuring device according to claim 28, wherein the base plate has a thickness of less than or equal to 1 cm.

* * * * *